US010827918B1

(12) United States Patent
Nuriel et al.

(10) Patent No.: US 10,827,918 B1
(45) Date of Patent: Nov. 10, 2020

(54) SYSTEM AND METHOD FOR AUTOMATICALLY EVALUATING A VISION OF A USER

(71) Applicant: SHAMIR OPTICAL INDUSTRY LTD., Upper Galilee (IL)

(72) Inventors: Devora Nuriel, Yesod Hamaaleh (IL); Noam Baran, Kibbutz Shamir (IL); Yotam Gil, Qiryat Tivon (IL); Liron Gleser, Rosh Pinna (IL)

(73) Assignee: SHAMIR OPTICAL INDUSTRY LTD., Kibbutz Shamir (IL)

( * ) Notice: Subject to any disclaimer, the term of this patent is extended or adjusted under 35 U.S.C. 154(b) by 0 days.

(21) Appl. No.: 16/726,859

(22) Filed: Dec. 25, 2019

(51) Int. Cl.
  *A61B 3/024* (2006.01)
  *A61B 3/028* (2006.01)
  *A61B 3/00* (2006.01)
  *A61B 3/08* (2006.01)
  *A61B 3/02* (2006.01)

(52) U.S. Cl.
  CPC .......... *A61B 3/024* (2013.01); *A61B 3/0091* (2013.01); *A61B 3/022* (2013.01); *A61B 3/028* (2013.01); *A61B 3/08* (2013.01)

(58) Field of Classification Search
  CPC ...................................................... A61B 3/024
  USPC ................................................................ 351/209
  See application file for complete search history.

(56) References Cited

U.S. PATENT DOCUMENTS

2019/0102904 A1   4/2019   Odagiri et al.
2019/0269315 A1*  9/2019   Lu .......................... A61B 3/024

FOREIGN PATENT DOCUMENTS

| CN | 109758111 | 5/2019 |
| WO | WO19145954 | 1/2019 |
| WO | WO19109058 | 6/2019 |

* cited by examiner

*Primary Examiner* — James C. Jones
(74) *Attorney, Agent, or Firm* — Pearl Cohen Zedek Latzer Baratz LLP

(57) ABSTRACT

A method of automatically evaluating vision of the user may include: subsequently displaying, by the processing unit, on a display, a subset of stimuli of a plurality of stimuli; tracking, by a gaze tracking device, a gaze of the user with respect to at least some of the stimuli of the subset being displayed on the display; obtaining multiple gaze datasets, at least one gaze dataset for at least some of the stimuli of the subset being displayed; and evaluating, by the processing unit, the vision of the user based on at least one of the multiple gaze datasets.

20 Claims, 12 Drawing Sheets

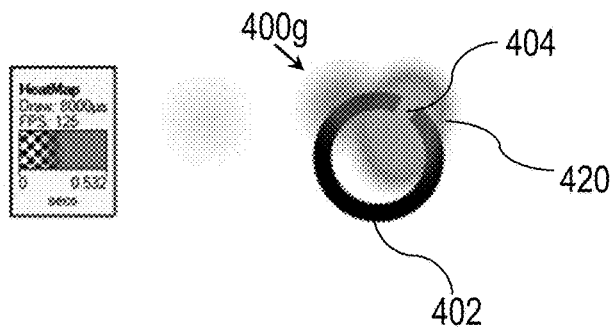
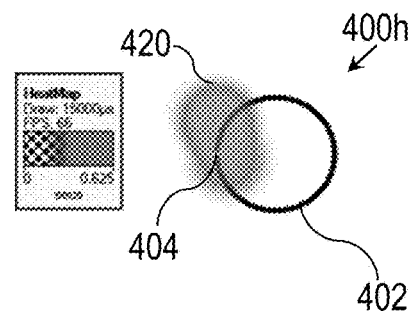
Fig. 4G
Fig. 4H
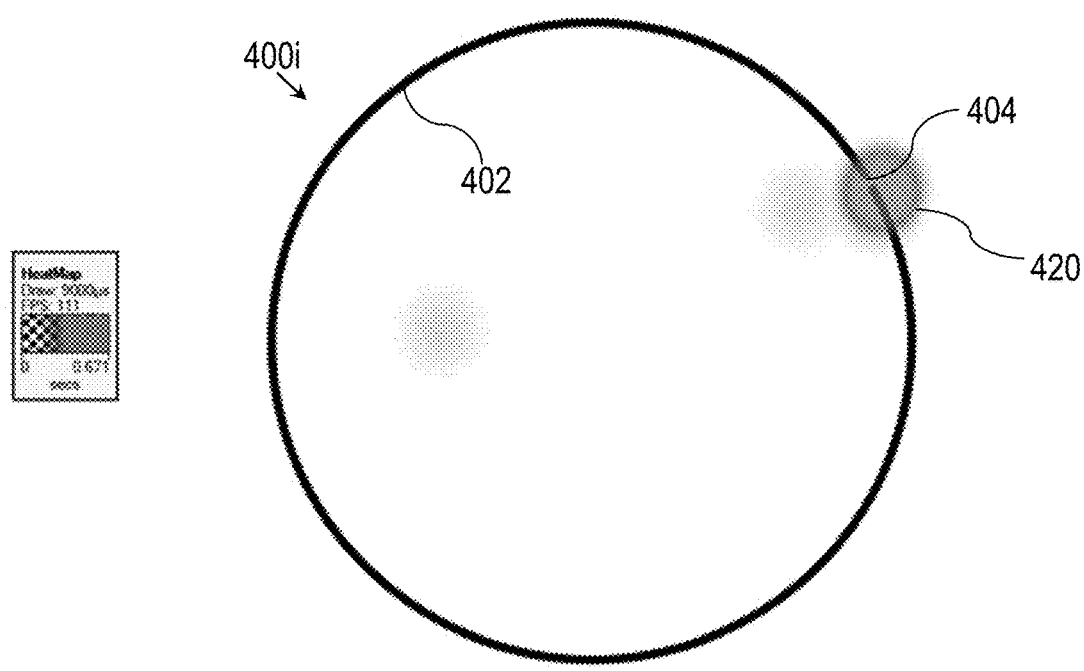
Fig. 4I
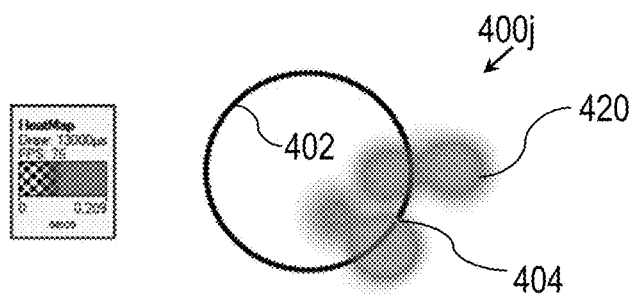
Fig. 4J

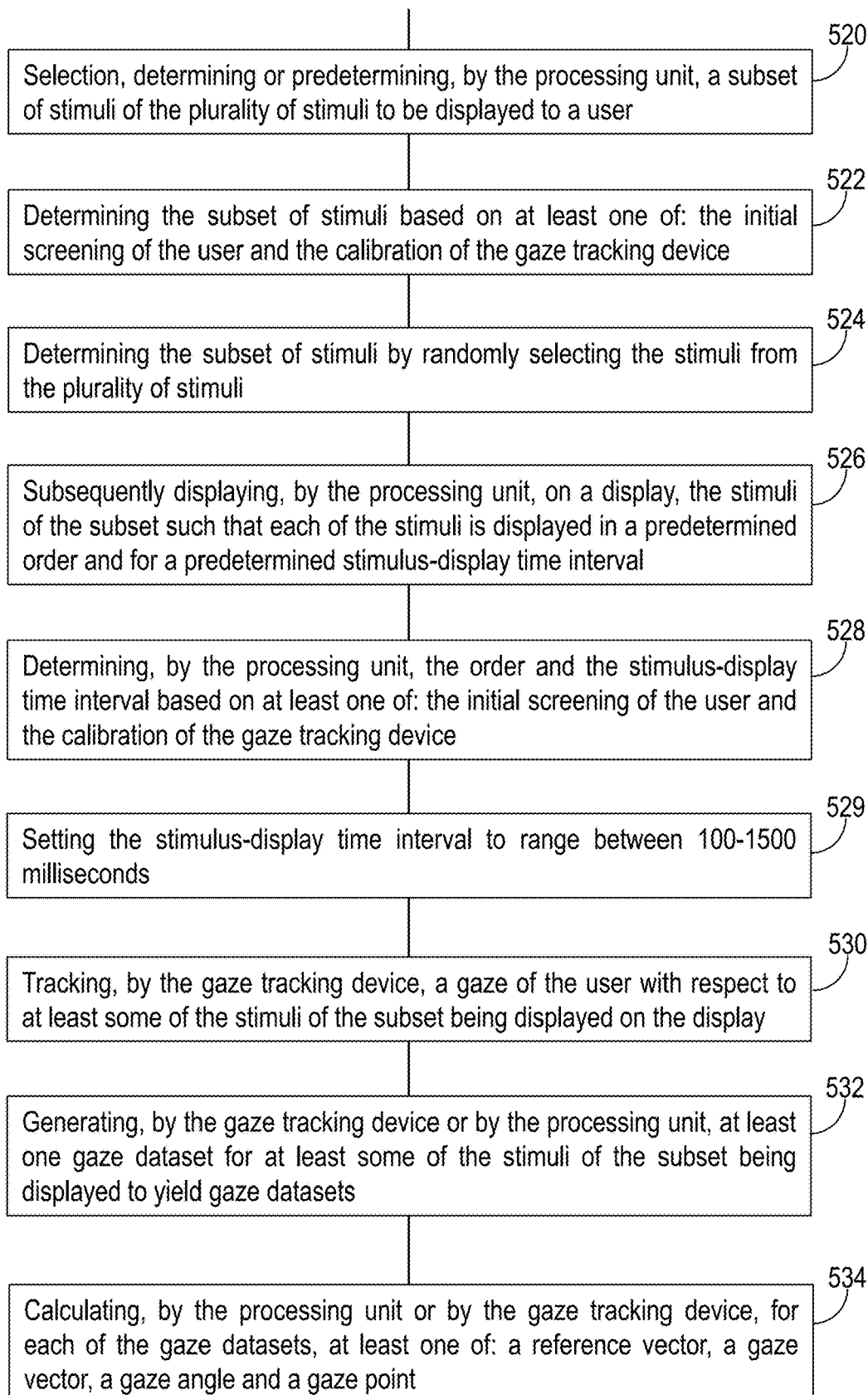
Fig. 5 (cont. 1)

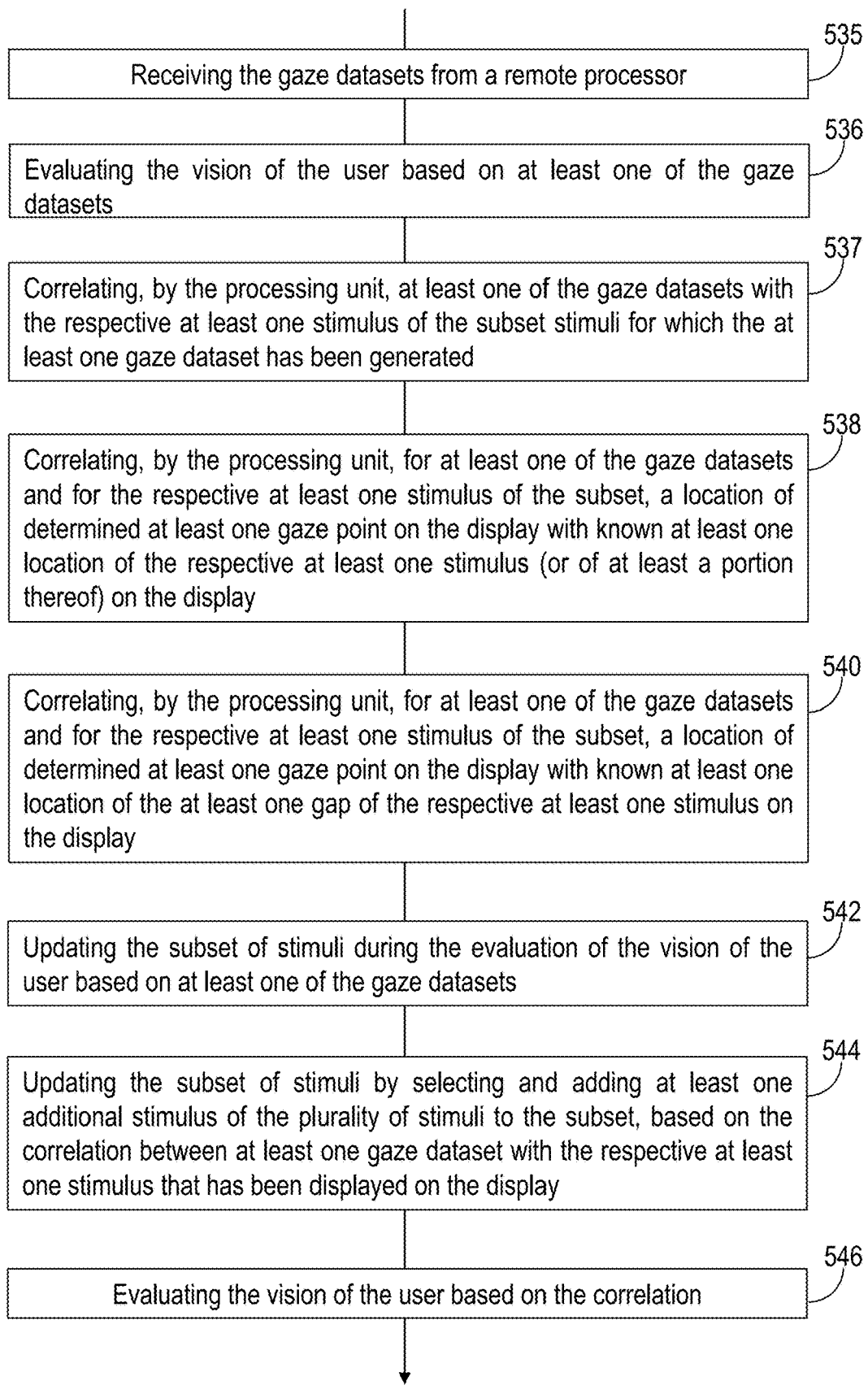
Fig. 5 (cont. 2)

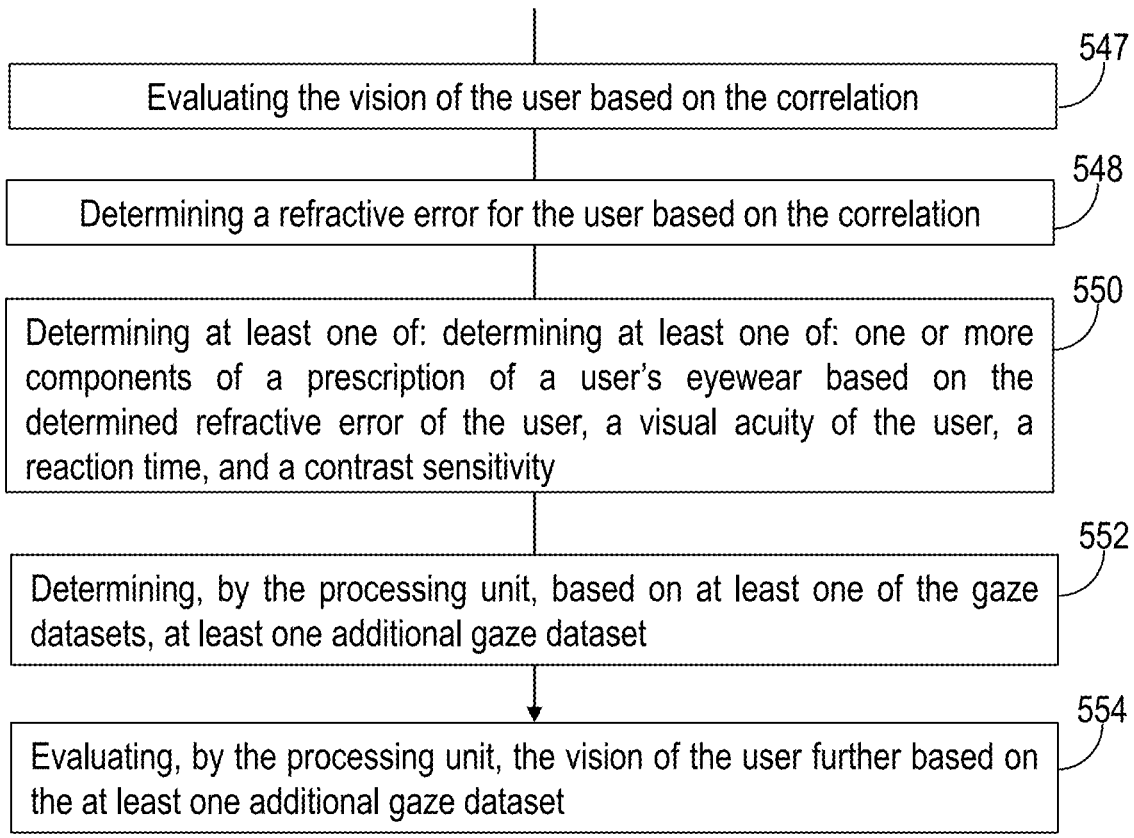
Fig. 5 (cont. 3)

US 10,827,918 B1

SYSTEM AND METHOD FOR AUTOMATICALLY EVALUATING A VISION OF A USER

FIELD OF THE INVENTION

The present invention relates to the field of ophthalmology and, more particularly, to systems and methods for automatically evaluating a vision of a user.

BACKGROUND OF THE INVENTION

Current electronic systems for evaluation of a vision of a user typically require an active feedback from the user in response to stimuli being displayed on a display. The systems further evaluate the vision of the user based on the feedback thereof.

One disadvantage of current electronic systems for evaluation of a vision of a user is that such systems are not objective. For example, the user is typically required to respond whether the user did observe the stimuli or did not observe the stimuli. However, each user may interpret these optional answers in a different manner as compared to other users. Accordingly, the evaluation of the vision of the user may be affected by a subjective interpretation of the stimuli by the user.

Another disadvantage of current electronic systems for evaluation of a vision of a user is that such systems typically support a binary feedback only. For example, the user is typically required to respond whether the user did observe the stimuli or did not observe the stimuli. However, the evaluation of the vision is not discrete and may have multiple phases.

Another disadvantage of current electronic systems is that waiting for the user to provide feedback increases the overall duration of the evaluation and increases the fatigue of the user, which can in-turn impact the results of the evaluation.

Another disadvantage of current electronic systems for evaluation of a vision of a user is that such systems typically require the user to provide a feedback in response to stimuli displayed on a display, which in turn requires a cognitive action. As a result, the evaluation of the vision of the user may be affected by a cognitive condition of the user.

Another disadvantage of current electronic systems for evaluation of a vision of a user is that such systems may have high false positive and/or high false negative errors. For example, the user may confuse input gestures with respect to predetermined input instructions (e.g., click Yes instead of No, etc.).

SUMMARY OF THE INVENTION

Some aspects of the present invention may provide a method of automatically evaluating vision of the user, the method may include: displaying, by the processing unit, on a display, a subset of stimuli of a plurality of stimuli such that each of the stimuli is displayed for a predetermined stimulus-display time interval; tracking, by a gaze tracking device, a gaze of the user with respect to at least some of the stimuli of the subset being displayed on the display; obtaining multiple gaze datasets, at least one gaze dataset for at least some of the stimuli of the subset being displayed; and evaluating, by the processing unit, the vision of the user based on at least one of the multiple gaze datasets.

Some embodiments may include correlating, by the processing unit, at least one of the multiple gaze datasets with the respective at least one stimulus of the subset stimuli for which the at least one gaze dataset has been generated; and evaluating the vision of the user based on the correlation thereof.

Some embodiments may include obtaining the multiple gaze datasets by at least one of: calculating the multiple gaze datasets by the processing unit, calculating the multiple gaze datasets by the gaze tracking device; and receiving the multiple gaze datasets from a remote processor.

Some embodiments may include evaluating the vision of the user by determining at least one of: one or more components of a prescription of a user's eyewear based on the determined refractive error of the user, a visual acuity of the user, a reaction time, and a contrast sensitivity.

Some embodiments may include: performing, by the processing unit, an initial screening of a user to obtain a personal information of the user; and determining at least one of: the subset of the stimuli, the order in which the stimuli to be displayed and the stimulus-display time interval, based on the initial screening of the user.

Some embodiments may include updating, by the processing unit, the subset of stimuli by selecting and adding at least one additional stimulus of the plurality of stimuli to the subset, based on at least one of the multiple gaze datasets.

Some embodiments may include setting, by the processing unit, the stimulus-display time interval to range between 100-1500 milliseconds.

Some embodiments may include defining the stimuli such that each of the stimuli includes at least one line and at least one gap along the at least one line.

Some embodiments may include defining the stimuli such that a ratio of a stimulus dimension of each of at least some of the stimuli over a size of the at least one gap thereof ranges between 1/50-1/10.

Some embodiments may include: correlating, by the processing unit, for at least one of the gaze datasets and for the respective at least one stimulus of the subset, a location of a determined at least one gaze point on the display with known at least one location of the at least one gap of the respective at least one stimulus on the display; and evaluating the vision of the user based on the correlation thereof.

Some aspects of the present invention may provide a system for automatically evaluating a vision of the user, the system may include: a display capable to display stimuli of a subset such that each of the stimuli is displayed in a predetermined order and for a predetermined stimulus-display time interval; a gaze tracking device to track a gaze of the user with respect to at least some of the stimuli of the subset being displayed on the display, and a processing unit to: obtain multiple gaze datasets, at least one gaze dataset for at least some of the stimuli of the subset being displayed, and evaluate the vision of the user based on at least one of the multiple gaze datasets.

In some embodiments, the processing unit is configured to: correlate at least one of the multiple gaze datasets with the respective at least one stimulus of the subset stimuli for which the at least one gaze dataset has been generated; and evaluate the vision of the user based on the correlation thereof.

In some embodiments, the processing unit is configured to obtain the multiple gaze datasets by at least one of: calculating the multiple gaze datasets, receiving the multiple gaze datasets from the gaze tracking device, and receiving the multiple gaze datasets from a remote processor.

In some embodiments, the processing unit is configured to determine at least one of: one or more components of a prescription of a user's eyewear based on the determined refractive error of the user, a visual acuity of the user, a reaction time, and a contrast sensitivity.

In some embodiments, the processing unit is configured to: perform an initial screening of a user to obtain a personal information of the user; and determine at least one of: the subset of the stimuli, the order in which the stimuli to be displayed and the stimulus-display time interval, based on the initial screening of the user.

In some embodiments, the processing unit is configured to update the subset of stimuli by selecting and adding at least one additional stimulus of the plurality of stimuli to the subset, based on at least one of the multiple gaze datasets.

In some embodiments, the processing unit is configured to set the stimulus-display time interval to range between 100-1500 milliseconds.

In some embodiments, each of the stimuli may include at least one line and at least one gap along the at least one line.

In some embodiments, a ratio of a stimulus dimension of each of at least some of the stimuli over a size of the at least one gap thereof ranges between 1/50-1/10.

In some embodiments, the processing unit is configured to: correlate, by the processing unit, for at least one of the gaze datasets and for the respective at least one stimulus of the subset, a location of determined at least one gaze point on the display with known at least one location of the at least one gap of the respective at least one stimulus on the display; and evaluate the vision of the user based on the correlation thereof.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings:

FIGS. 4G, 4H, 4I, 4J, 4K, 4L, 4M, 4N, 4O, 4P, 4Q, 4R, 4S and 4T are schematic illustrations of various configurations of stimuli accompanied with respective gaze points distributions, according to some embodiments of the invention.

Figure 1:
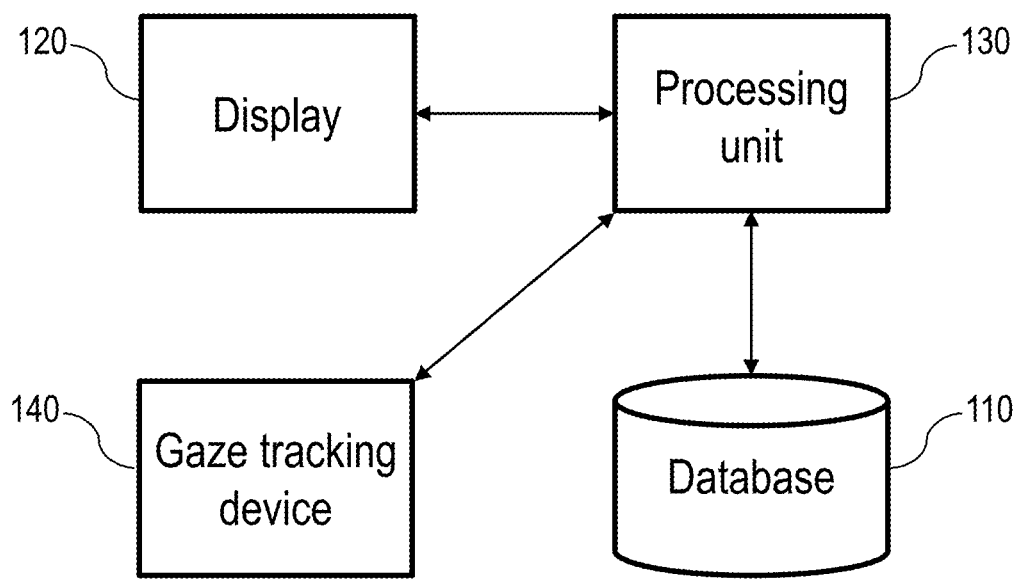
FIG. 1 is a schematic block diagram of a system for automatically evaluating a vision of a user, according to some embodiments of the invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor.

Reference is now made to FIG. 1, which is a schematic block diagram of a system 100 for automatically evaluating a vision of a user, according to some embodiments of the invention.

According to some embodiments, system 100 may include a database 110, a display 120, a processing unit 130 in communication with database 110 and display 120, and a gaze tracking device 140 in communication with processing unit 130.

Database 110 may include a plurality of stimuli, or parameters required to render the stimuli. The stimuli may, for example, include optotypes. Examples of optotypes according to various embodiments of the invention are described below with respect to FIGS. 4A, 4B, 4C, 4D, 4E and 4F.

Processing unit 130 may select, determine or predetermine a subset of stimuli of the plurality of stimuli to be displayed to a user. Processing unit 130 may further display the stimuli of the subset on a display 120. Display 120 may, for example, be a digital display such as a LED display, a computer screen, a television, a mobile device, etc. Processing unit 130 may display the stimuli of the subset in a controlled manner. For example, processing unit 130 may sequentially display the stimuli of the subset in a predetermined order, wherein each of the stimuli may be displayed for a predetermined stimulus-display time interval. Processing unit 130 may, for example, display the stimuli in an adaptive manner that may be dependent on, for example, a user's response to previously displayed stimuli, such that the subset may be changed throughout the test. The user's response may subsequently be analyzed and compared with stored data in database 110. The test may be repeated until, for example, a decision that reliable data is achieved is made, by, for example, comparing it with database 110 and determining whether there is a sufficient number of correct responses so as to make a decision with high confidence.

A user (which is not shown in FIG. 1 for sake of clarity) may be located at a predetermined distance from display 120. The distance of the user from display 110 may be determined by, for example, processing unit 130 (e.g., based on images obtained by a camera of system 100 or by a camera that may be part of gaze tracking device). The user may view the stimuli of the subset being displayed on display 120, and a gaze of the user may move with respect to display 120 accordingly.

Gaze tracking device 140 may track the gaze of the user with respect to at least some of the stimuli of the subset being displayed on display 120. In various embodiments, gaze tracking device 140 or processing unit 130 may generate at least one gaze dataset for at least some of the stimuli of the subset being displayed to yield multiple gaze datasets. In some other embodiments, the at least one gaze dataset may be generated by a remote processor (e.g., such as a cloud, etc.) based on readings of gaze tracking device. Each of the multiple gaze datasets may, for example, include at least one of: a reference vector, a gaze vector, a gaze angle and a gaze point (e.g., as described below with respect to FIG. 3). In some embodiments, at least some of the multiple gaze datasets may include the pupil size of the user.

Processing unit 130 may evaluate the vision of the user based on at least one of the gaze datasets.

In some embodiments, processing unit 130 may apply one or more artificial intelligence (AI) methods on at least one of the gaze datasets. For example, the least one of the gaze datasets may be inputted into one or more pre-trained neural network that may output the evaluated vision of the user.

In some other embodiments, processing unit 130 may correlate at least one of the gaze datasets with the respective at least one stimulus of the subset (e.g., the stimulus/stimuli for which the at least one gaze dataset has been generated). For example, processing unit 130 may correlate, for at least one of the gaze datasets and for the respective at least one stimulus of the subset, a location of determined gaze point(s) (e.g., indicating an intersection of gaze vector(s) on display 120, as described below with respect to FIG. 3) with known location(s) of the respective at least one stimulus (or specified portion(s) thereof) on display 120. Processing unit 130 may further evaluate the vision of the user based on the correlation thereof.

For example, processing unit 130 may determine a refractive error for the user. In another example, processing unit 130 may determine a prescription, or one of the components of the prescription, for a user's eyewear (e.g., based on the determined refractive error of the user). The components of the prescription (commonly referred to as Rx) may, for example, be Sphere (Sph), Cylinder or astigmatism (Cyl), Axis (Ax), Vertical and Horizontal prism, and Addition (Add). In another example, processing unit 130 may determine the Visual Acuity (VA) of the user. Other vision evaluation measurements may be determined, including, for example, reaction time, contrast sensitivity, and other vision parameters.

In some embodiments, processing unit 130 may calibrate gaze tracking device 140. For example, the calibration may be performed for each user, for example prior to actual evaluation of the vision thereof (e.g., prior to testing the user). During the calibration stage, processing unit 130 may instruct the user to look at one or more known calibration locations on display 120 (e.g., by displaying respective instructions to the user on display 120), while gaze tracking device 140 may track the gaze of the user with respect to the known calibration location(s) and generate one or more calibration datasets. Processing unit 130 may further calibrate gaze tracking device 140 based on the calibration dataset(s). The calibration may, for example, improve an accuracy of the gaze datasets being generated by gaze tracking device 140 and/or by processing unit 130.

In some embodiments, processing unit 130 may perform an initial screening of the user. The initial screening may be performed by, for example, obtaining a personal information of the user. For example, processing unit 130 may display predetermined questions on display 120 and receive answers from the user (e.g., via a user interface). The personal information may, for example, include information concerning whether the user is near sighted or far sighted, information concerning previous vision evaluations (e.g., previous refractive error measurements), an age of the subject, etc. This data may be saved to the database 110.

In some embodiments, processing unit 130 may determine the subset of the stimuli to be displayed to the user based on the initial screening and the gathered personal information of the user. Optionally, processing unit 130 may determine the subset of the stimuli to be displayed to the user also based on the calibration results.

For example, processing unit 130 may select for each user and based on the initial screening thereof (and optionally based on the calibration) which of the plurality of the stimuli from database 110 are to be included within the subset of the stimuli, determine an order of the stimuli in the subset and/or determine the stimulus-display time interval during which each of the stimuli of the subset to be displayed.

In some embodiments, the stimulus-display time interval may range between 100-1500 milliseconds. For example, the stimulus-display time interval may be 300 milliseconds. In general, the stimulus-display time interval, for example as determined by processing unit 130, may be long enough to obtain a significant number of gaze datasets for each stimulus, but not long enough for the user to adapt and accommodate in order to improve their perception of the stimulus.

In some other embodiments, processing unit 130 may randomly select the stimuli of the plurality of stimuli stored in database 110 to form the subset to be displayed to the user.

In some embodiments, processing unit 130 may update the subset of stimuli during the evaluation of the vision of the user. The subset of the stimuli may be updated based on, for example, at least one of the gaze datasets. For example, processing unit 130 may select and add at least one additional stimulus of the plurality of stimuli to the subset, based on correlation between at least one gaze dataset with the respective at least one stimulus that has been displayed on the display. In this manner, the subset of stimuli may be updated using an adaptive psychophysical procedure, wherein one or more new stimuli to be displayed are selected based on the response of the user to one or more previous stimuli that have been displayed. For example, the one or more newly selected/additional stimuli may have different stimulus parameters as compared to the stimuli that have been initially selected. Such stimulus parameters may, for example, include type of the stimulus, geometrical parameters of the stimulus (e.g., such as dimensions, thickness, gap size, etc.), etc. For example, if processing unit 130 determines that the user is capable of observing stimuli of a specified size, processing unit 130 may update the subset of the stimuli by adding stimuli that are smaller than the stimuli that have been initially selected.

In some embodiments, at least some data obtained by system 100 for the user may be stored in database 110. Such data may, for example, include a user metadata, user gaze datasets (per stimuli displayed), a user refractive error, a Rx (e.g., after evaluation), etc.

Figure 2:
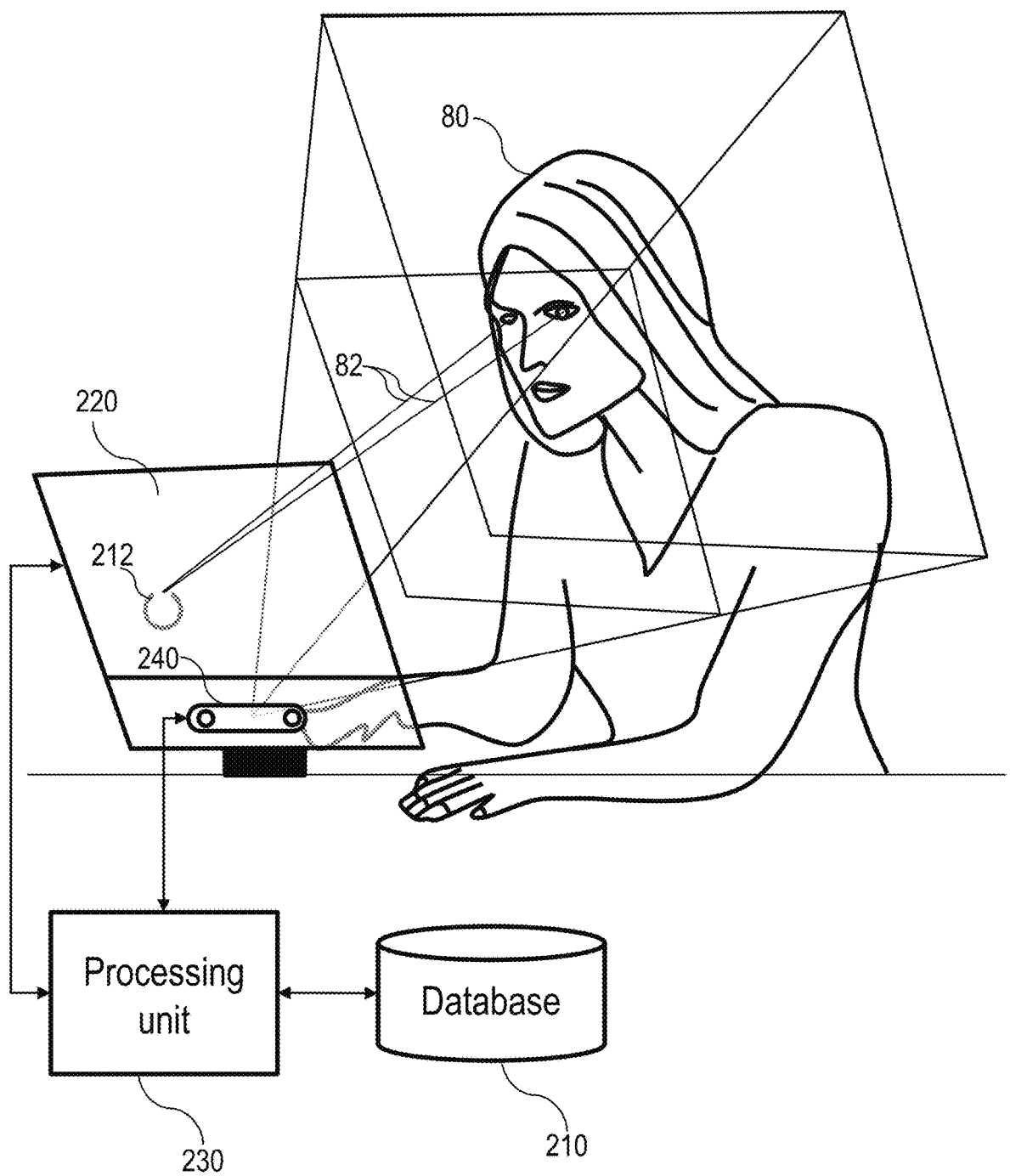
FIG. 2 is a schematic illustration of a more detailed aspect of a system for automatically evaluating a vision of user, according to some embodiments of the invention.

Reference is now made to FIG. 2, which is a schematic illustration of a more detailed aspect of a system 200 for automatically evaluating a vision of user 80, according to some embodiments of the invention.

According to some embodiments, system 200 may include a database 210, a display 220, a processing unit 230 and a gaze tracking device 240. Database 210, display 220, processing unit 230 and gaze tracking device 240 may be similar to database 110, display 120, processing unit 130 and gaze tracking device 140, respectively, as described above with respect to FIG. 1.

Database 210 may include a plurality of stimuli (e.g., optotypes). Processing unit 230 may select, determine or predetermine a subset of stimuli of the plurality of stimuli and to display the stimuli of the subset on display 220. For example, FIG. 2 shows stimulus 212 of the subset being displayed on display 220. Gaze tracking device 240 may track the gaze of the user with respect to at least some of the stimuli of the subset being displayed on display 220. Gaze tracking device 240 or processing unit 230 (or optionally a remote processor) may determine at least one gaze dataset for at least some of the stimuli of the subset being displayed to yield multiple gaze datasets. Processing unit 230 may correlate at least one of the gaze datasets with the respective stimuli of the subset and evaluate the vision of the user based on the correlation thereof (e.g., as described above with respect to FIG. 1).

In some embodiments, gaze tracking device 240 may include one or more cameras (e.g., as schematically shown in FIG. 2). In some embodiments, gaze tracking device 240 may include one or more illuminators (e.g., as schematically shown in FIG. 2). In some other embodiments, gaze tracking device 240 may rely on one or more external illuminators. In operation, the illuminator(s) may create one or more patterns of light on the eyes of user 80. The camera(s) of gaze tracking device 240 may take one or more images of the eyes of user 80 and the pattern(s) of light generated by illuminator(s).

In some embodiments, system 200 may include a non-transitory computer readable medium. The non-transitory computer readable medium may include one or more subsets of instructions that, when executed, cause a processor of gaze tracking device 240 or processing unit 230 of system 200 to generate the gaze datasets based on, for example, the images obtained by the camera(s) of gaze tracking device 240 (e.g., gaze datasets as described above with respect to FIG. 1 and below with respect to FIG. 3).

It is noted that FIG. 2 shows one example of gaze tracking device 240. However, other gaze tracking devices may be used as well. For example, in some other embodiments, gaze tracking device 240 may include two infrared cameras and one or more infrared illuminators. In some other embodiments, gaze tracking device 240 may include one camera and one or more illuminators with structured light. In some other embodiments, gaze tracking device 240 may include a single camera (e.g., camera integrated in a mobile device). In some other embodiments, gaze tracking device 240 may be wearable by user 80 (e.g., gaze tracking device 140 may include a head-mounted camera).

In some embodiments, gaze tracking device 240 may operate at a frequency of at least 25-30 Hz. In various embodiments, gaze tracking device 240 may have an accuracy of no more than 1 degree for a gaze angle and/or of no less that 1 mm for a gaze point (e.g., as calculated for the stimulus being displayed on display 220).

As would be apparent to those of ordinary skill in the art, each of database 210, display 220, processing unit 230 and/or gaze tracking device 240 may be implemented on its own device, a single device, or a combination of devices. For example, database 210, display 220 and/or processing unit 230 may be implemented on a single computing device (e.g., on a personal computed device such as laptop). The communication between database 210, display 220, processing unit 230 and/or gaze tracking device 240 may be wired and/or wireless.

Figure 3:
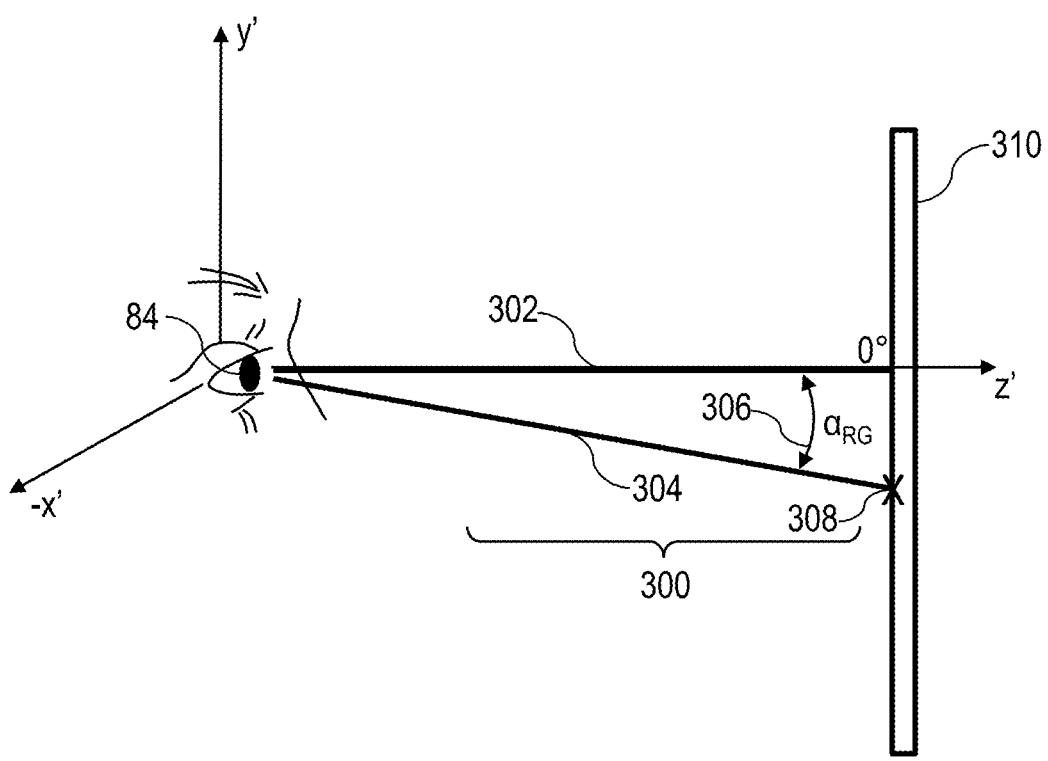
FIG. 3 is a schematic illustration of components of gaze dataset generatable by a gaze tracking device or by a processing unit of a system for automatically evaluating a vision of a user, according to some embodiments of the invention.

Reference is now made to FIG. 3, which is a schematic illustration of components of gaze dataset 300 generatable by a gaze tracking device or by a processing unit of a system for automatically evaluating a vision of a user, according to some embodiments of the invention.

FIG. 3 depicts certain components of gaze dataset 300 in a three-dimensional (3D) arbitrary coordinate system X', Y', Z'. In some embodiments, gaze dataset 300 may be generated by a gaze tracking device (e.g., such as gaze tracking devices 140, 240, as described above with respect to FIGS. 1, 2, respectively). In some other embodiments, gaze dataset 300 may be generated by a processing unit (e.g., such as processing units 130, 230, as described above with respect to FIGS. 1, 2, respectively) of a system for automatically evaluating a vision of a user (e.g., such as systems 100, 200, as described above with respect to FIGS. 1, 2, respectively). In some other embodiments, gaze dataset 300 may be generated by a remote processor (e.g., on a cloud, etc.). For example, gaze dataset 300 may be generated based on one or more images obtained by the gaze tracking device (e.g., as described above with respect to FIG. 2).

In some embodiments, gaze dataset 300 may include at least one of: a reference vector 302, a gaze vector 304, a gaze angle 306 and a gaze point 308 (e.g., as shown in FIG. 3).

Reference vector 302 may extend from an eye 84 of the user and may be perpendicular (or substantially perpendicular) to a display 310 on which the stimuli are being displayed. Display 310 may be similar to, for example, display 120, 220 described above with respect to FIGS. 1, 2, respectively.

Gaze vector 304 may extend from eye 84 of the user in a direction of the gaze of eye 84 of the user (or substantially in the direction thereof). Gaze vector 304 may indicate an extent of eye rotation of the user.

Gaze angle 306 (also indicated in FIG. 3 as $\alpha_{RG}$) may be an angle between gaze vector 304 and reference vector 302 (e.g., as shown in FIG. 3). Gaze angle 306 may have a horizontal component (e.g., in a direction of X' axis of the X'-Y'-Z' coordinate system) and a vertical component (e.g., in a direction of Y' axis of the X'-Y'-Z' coordinate system). In some embodiments, gaze angle 306 may be monocular (e.g., measured/determined independently for right eye and left eye of the user).

Gaze point 308 may be a point (e.g., 3D point) at which gaze vector 304 may intersect display 310 on which the stimuli are being displayed. Gaze point 308 may indicate a precise position that the user has been viewing at a time of the measurement. In various embodiments, gaze point 308 may be monocular or binocular. The monocular gaze point 308 may be measured/determined independently for the right eye and the left eye of the user. The binocular eye gaze point 308 may be determined as, for example, an average position between the monocular gaze points 308 determined independently for right eye and left eye of the user.

Reference is now made to FIGS. 4A, 4B, 4C, 4D, 4E and 4F, which are schematic illustrations of various configurations of stimuli 400 for a system for automatically evaluating a vision of a user, according to some embodiments of the invention.

FIGS. 4A, 4B, 4C, 4D, 4E and 4F depict examples of various stimuli (collectively referred hereinafter as stimuli 400). Stimuli 400 may be used in a system for automatically evaluating the vision of the user (e.g., system 100, 200 as described above with respect to FIGS. 1 and 2, respectively). Stimuli 400 may be rendered on a display of the system and/or stored in a database of the system (e.g., such as database 110, 120 described above with respect to FIGS. 1 and 2).

In some embodiments, each of stimuli 400 may include at least one line 402 and at least one gap 404 along at least one line 402 thereof. In embodiments shown in FIGS. 4A, 4B, 4C, 4D, 4E and 4F, the user may be instructed to look for gaps 404 in stimuli 400 when the stimuli are displayed on the display of the system (e.g., display 120, 220 as described above with respect to FIGS. 1 and 2).

Figure 4A:
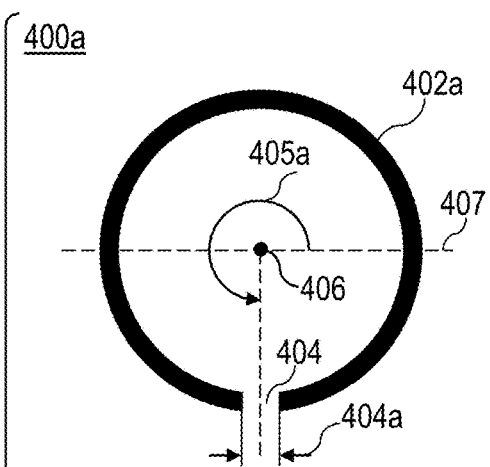
FIGS. 4A, 4B, 4C, 4D, 4E and 4F are schematic illustrations of various configurations of stimuli for a system for automatically evaluating a vision of a user, according to some embodiments of the invention.
Figure 4B:
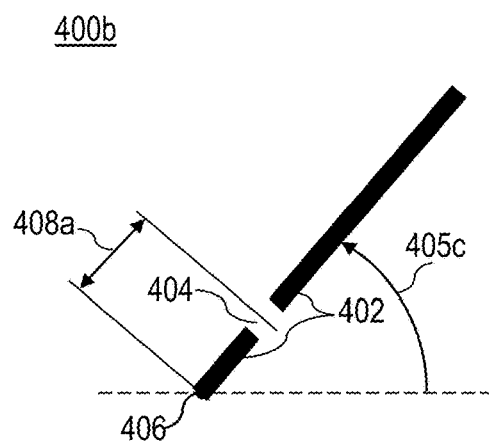

In various embodiments, line(s) 402 of each of stimuli 400 may be straight or shaped into a predefined shape (e.g., circle, ellipse, rectangle, etc.). For example, FIG. 4A depicts a first stimulus 400a in which line 402 is shaped into a circular shape (or substantially circular shape). In another example, FIG. 4B depicts a second stimulus 400b in which line 402 is straight (or substantially straight). In some embodiments, line(s) 402 of different stimuli 400 may have different widths.

Figure 4C:
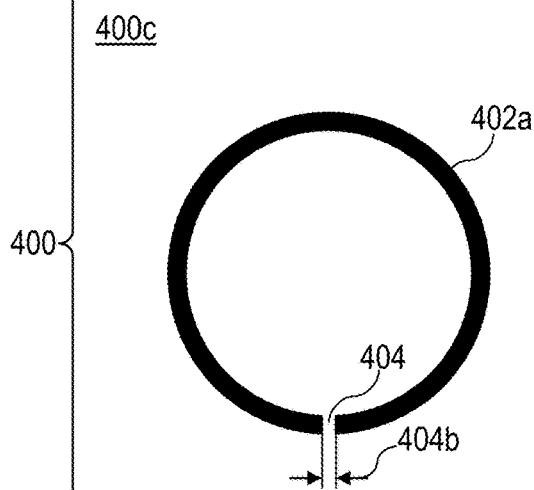

In some embodiments, gap(s) 404 of each of at least some of stimuli 400 may have a different size as compared to other stimuli 400. For example, FIG. 4C depicts a third stimulus 400c in which gap 404 has a second size 404b that is smaller than a first size 404a of gap 404 of first stimulus 400a depicted in FIG. 1A.

In various embodiments, gap(s) 404 of each of at least some of stimuli 400 may be positioned at a different angular position 405 with respect to a reference point 406 and a reference axis 407 of the stimulus as compared to other stimuli 400. For example, in first stimulus 400a depicted in FIG. 4A gap 404 is positioned at a first angular position 405a with respect to reference point 406 (e.g., a center point defined by curved line 402) and reference axis 407 thereof and in a fourth stimulus depicted in FIG. 4D gap 404 is positioned at a second angular position 405b with respect to reference point 406 and reference axis 407 thereof. In another example, in second stimulus 400b depicted in FIG. 4B gap 404 is positioned at a third angular position 405c with respect to reference point 406 (e.g., one of ends of straight line 402) and reference axis 407 thereof and in a fifth stimulus 400e depicted in FIG. 4E gap 404 is positioned at a fourth angular position 405d with respect to reference point 406 and reference axis 407 thereof.

In some embodiments, gap(s) 404 of each of at least some of stimuli 400 may be positioned at a different distance 408 along line(s) 402 with respect to reference point 406 of this stimulus as compared to other stimuli 400. For example, in second stimulus 400b depicted in FIG. 4B, gap 404 is positioned at a first distance 408a along line 402 with respect to reference point 406 thereof (e.g., one of the ends of straight line 402), and in a sixth stimulus 400f depicted in FIG. 4F, gap 404 is positioned at a second distance 408b along line 402 with respect to reference point 406 thereof.

In general, lines 402 of different stimuli 400 may have different shapes (e.g., circular, linear, elliptical, rectangular, etc.), different dimensions (e.g., lengths or diameters), and/or different thicknesses. Gaps 404 of different stimuli 400 may have different sizes. Gaps 404 of different stimuli may be disposed at different angular positions 405 with respect to reference point 406 and reference axis 407 of the stimulus. Gaps 404 of different stimuli may be disposed at different distances 408 along lines 402 with respect to reference point 406 of the stimulus. (e.g., as described above with respect to FIGS. 4A, 4B, 4C, 4D, 4E and 4F)

In some embodiments, a ratio of a stimulus dimension of each of stimuli 400 (e.g., diameter, length, etc. of the entire stimulus) over a size of gap 404 of the respective stimulus may be no more than 1/5. For example, the ratio may range between 1/50-1/10. In another example, the ratio may be 1/30. This in contrast to typical optotypes (e.g., Snellen-type optotypes, or Landolt C, widely used to determine the minimum perceivable angle of the gap is taken as measure of the visual acuity) that typically have the ratios of 1/5.

Such relatively high ratios of the stimulus dimension over the size of gap 404 thereof (e.g., ranging between 1/50-1/10) according to some embodiments of the invention may be due to, for example, a precision of a gaze tracking device of the system (e.g., such as gaze tracking device 140, 240 described above with respect to FIGS. 1 and 2, respectively), that may be between 0.5-3 millimeter on the display of the system thereof (e.g., such as display 120, 220 described above with respect to FIGS. 1 and 2, respectively). For example, if typical optotypes have been used in the system (e.g., such as Landolt C polytypes), the stimulus dimension of several millimeters would have been reached in many cases. Accordingly, the precision of the gaze tracking device would have not been high enough to determine which gaze points fall on gaps 404 of stimuli 400 and which do not, as an error in the measurements would have been too high.

In some embodiments, stimuli 400 may have a predetermined foreground color. In some embodiments, stimuli 400 may be displayed over a predetermined background color. In various embodiments, the foreground and/or background color can be modified throughout the evaluation, enabling high or low color contrast (or grayscale contrast) between the background and foreground. These colors, and the contrast between them, may be additional parameters that may be used to, for example, evaluate the contrast sensitivity of the user.

Reference is now made to FIGS. 4G, 4H, 4I, 4J, 4K, 4L, 4M, 4N, 4O, 4P, 4Q, 4R, 4S and 4T, which are schematic illustrations of various configurations of stimuli 400 accompanied with respective gaze points distributions 420, according to some embodiments of the invention.

FIGS. 4G, 4H, 4I, 4J, 4K, 4L, 4M, 4N, 4O, 4P, 4Q, 4R, 4S and 4T depict examples of various stimuli 400, wherein each of the depicted stimuli is accompanied by a respective gaze points distribution 420 (e.g., such as gaze points 308 described above with respect to FIG. 3).

In embodiments shown in FIGS. 4A, 4B, 4C, 4D, 4E and in FIGS. 4G, 4H, 4I, 4J, 4K, 4L, 4M, 4N, 4O, 4P, 4Q, 4R, 4S and 4T, the user may be instructed to look for gap(s) 404 of each stimulus being displayed on the display of the system (e.g., such as display 120, 220 described above with respect to FIGS. 1 and 2, respectively).

Accordingly, when the user is capable of observing gap 404 in a particular stimulus being displayed, a location of gaze point(s) on the display plane generated for this particular stimulus (e.g., such as gaze point 308 of gaze dataset 300 described above with respect to FIG. 3) may be in a predetermined vicinity of a location of gap 404 of this particular stimulus on the display (e.g., as shown in FIGS. 4G, 4H, 4I, 4K, 4N, 4P).

In the same manner, when the user is not capable of observing gap 404 in a particular stimulus being displayed, the location of gaze point(s) on the display plane generated for this particular stimulus may exceed beyond the predetermined vicinity of the location of gap 404 of this particular stimulus (e.g., as shown in FIGS. 4J, 4L, 4M, 4O, 4Q, 4R, 4S, 4T).

In some embodiments, a system for automatically evaluating a vision of a user (e.g., such as system 100, 200 described above with respect to FIGS. 1 and 2, respectively) may utilize stimuli 400 to perform the evaluation thereof. A database of the system (e.g., such as database 110, 210 described above with respect to FIGS. 1 and 2, respectively) may include a plurality of stimuli 400, such as stimuli 400.

A processing unit of the system (e.g., such as processing unit 130, 230 described above with respect to FIGS. 1 and 2, respectively) may select, determine or predetermine a subset of stimuli of the plurality of stimuli and display the stimuli of the subset on a display of the system (e.g., such as display 120, 220 described above with respect to FIGS. 1 and 2, respectively).

In some embodiments, the processing unit may determine the subset of the stimuli to be displayed to the user based on an initial screening and a personal information of the user, and optionally also based on the calibration results of a gaze tracking device of the system (e.g., as described above with respect to FIG. 1).

In some embodiments, the processing unit may determine each stimulus to be displayed using an adaptive method, depending on the feedback from the patient up to that point. For example, if the processor determines with high confidence that a particular gap size is perceived by the user (in one or more meridians), the processor may select a subsequent stimulus for display with a smaller gap size. Alternatively, the processor may determine with high confidence that a particular gap size is not perceived by the user, and the processor may select the subsequent stimulus with a larger gap size. Alternatively, the processor may determine with high confidence that a particular gap size is not perceived by the user in one meridian, and the processor may select the subsequent stimulus the same gap size in another meridian.

The processing unit may, for example, select for each user and based on the initial screening thereof (and optionally based on the calibration) which of the plurality of the stimuli from the database are to be included within the subset of the stimuli.

Figure 4D:
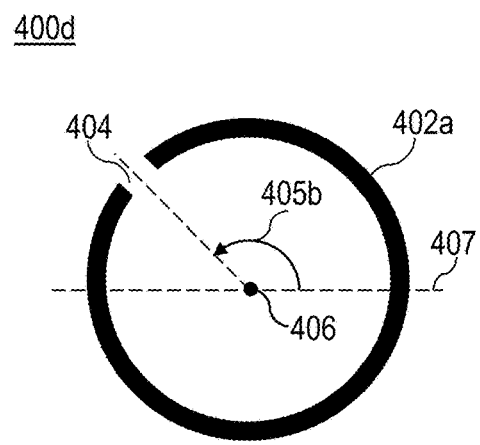
Figure 4E:
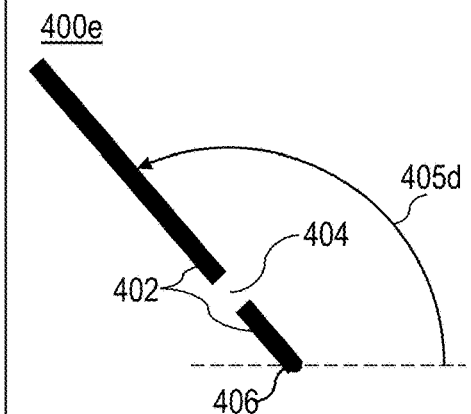
Figure 4F:
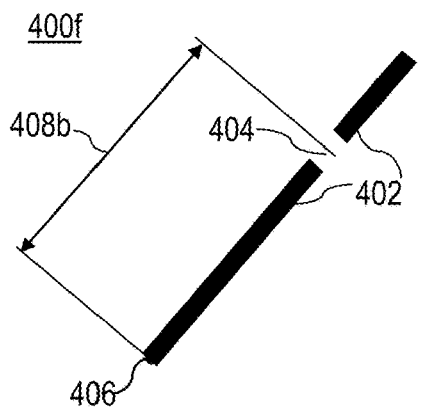
Figure 4K:
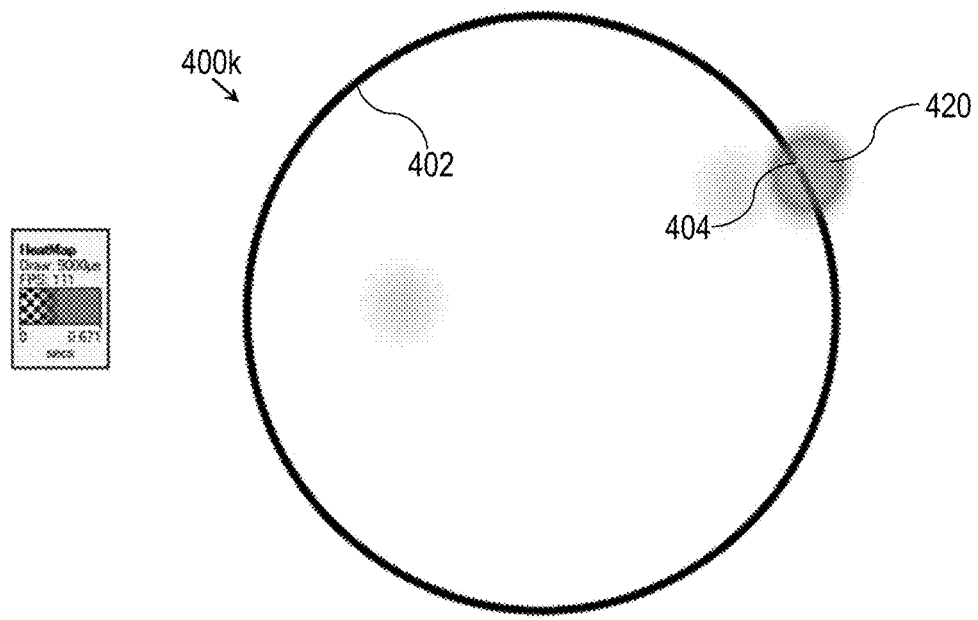
Figure 4L:
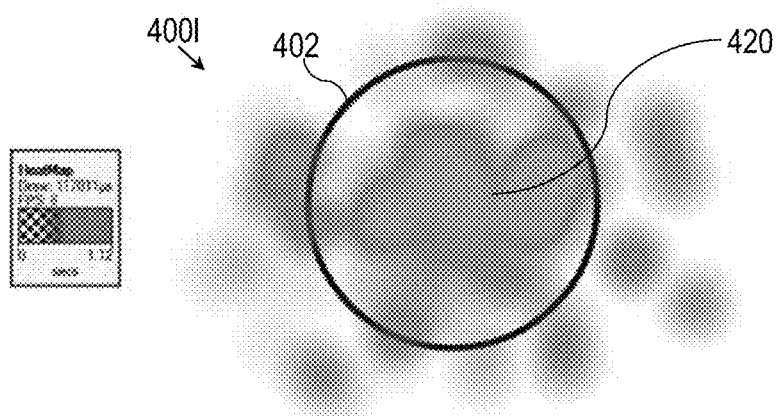
Figure 4M:
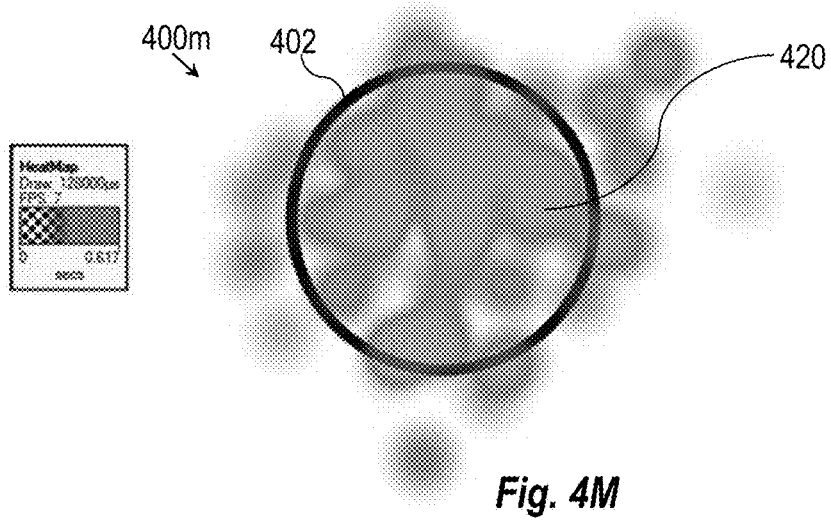
Figure 4P:
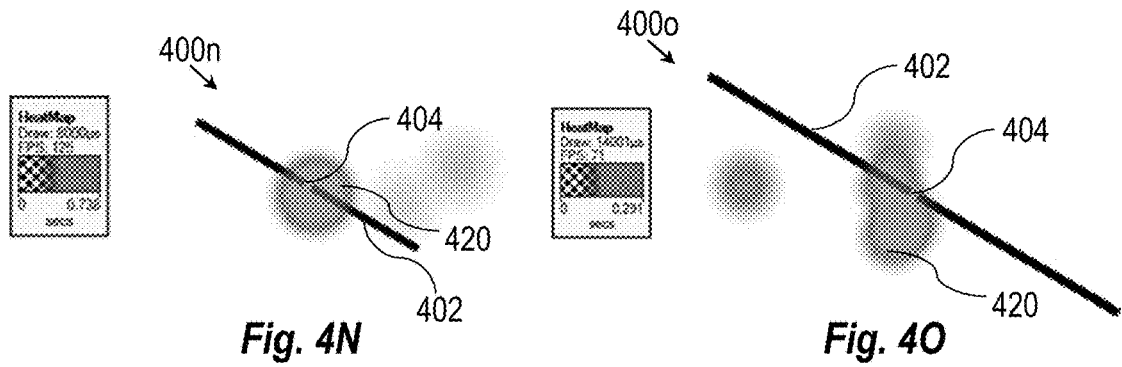
Figure 4P:
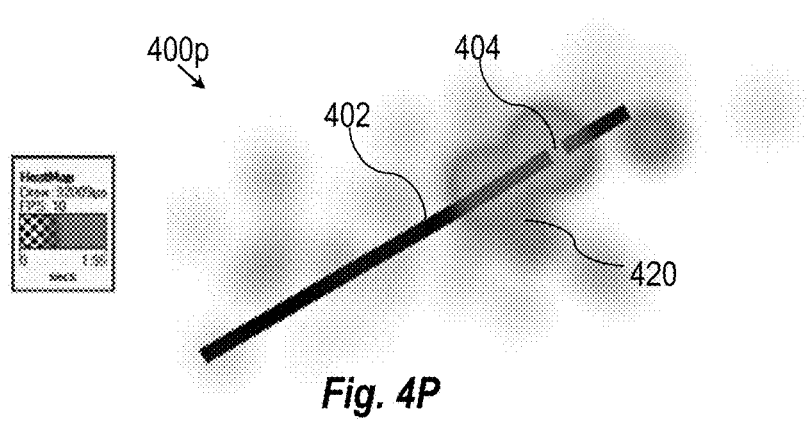
Figure 4Q:
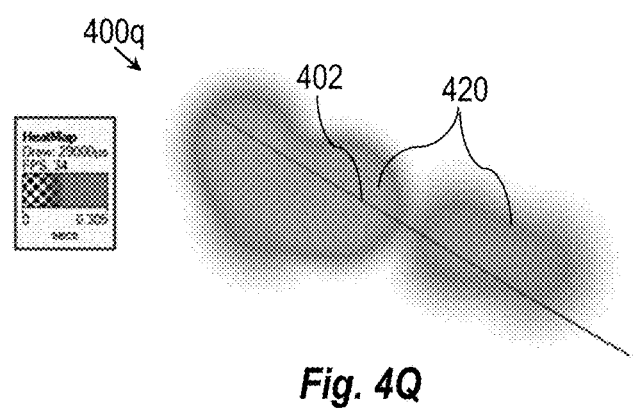
Figure 4R:
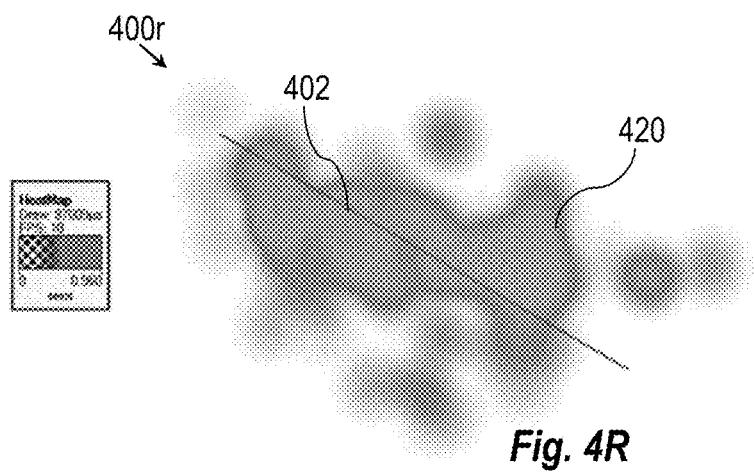
Figure 4S:
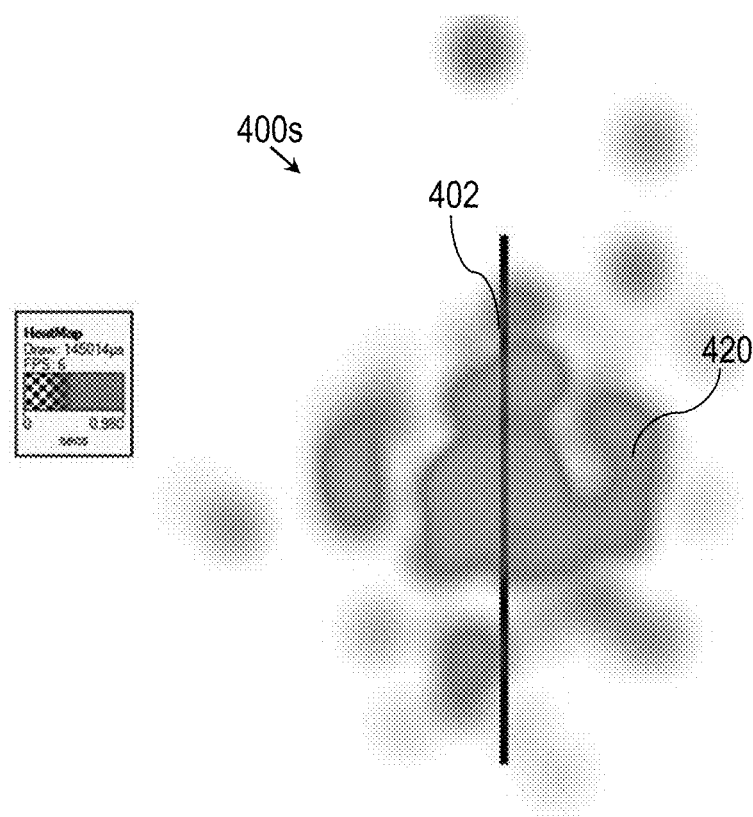
Figure 4T:
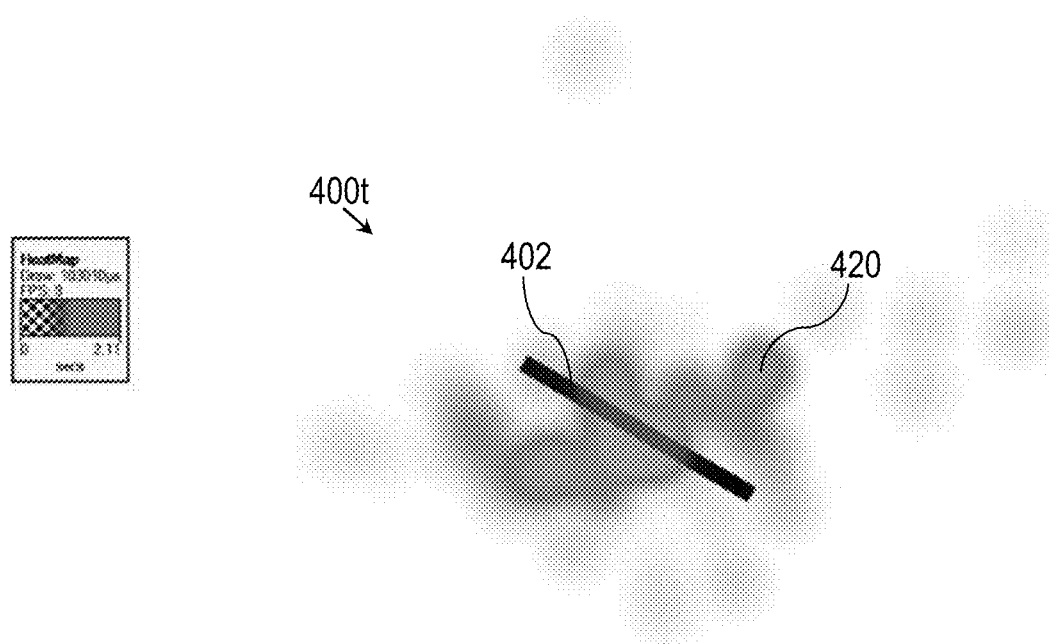

For example, the processing unit may determine the type of the stimuli to be included in the subset (e.g., stimuli having curved lines (e.g., as shown in FIGS. 4A, 4C, 4D) and/or straight lines (e.g., as shown in FIGS. 4B, 4E, 4F)).

In another example, the processing unit may determine the gaps range size (e.g., such as gaps 404) for the stimuli to be included in the subset, while, for example, maintaining the ratio of the stimulus dimension over the size of the respective gap 404 for the selected stimuli.

In another example, the processing unit may determine the gap angular position range (e.g., such as angular position 405 described above with respect to FIGS. 4A, 4D and FIGS. 4B, 4E) and/or the gap distance range (e.g., such as distance 408 described above with respect to FIGS. 4B, 4F) for the stimuli to be included in the subset.

The processing unit may, for example, determine an order of the stimuli in the subset in which the stimuli are to be displayed to the user. For example, the subset may include a first group of stimuli having a first size of the gap, wherein the stimuli of the first group may have different angular positions of the gaps thereof. Yet, in this example, the subset may include a second group of stimuli having a second size of the gap that is smaller than the first size, wherein the stimuli of the second group may yet have different angular positions of the gaps thereof. Yet, in this example, the stimuli of the first group may be first subsequently displayed to the user and then the stimuli of the second group may be subsequently displayed to the user, wherein each of the stimuli may be displayed for a predetermined stimulus-display time interval (e.g., ranging between 100-1500 milliseconds).

It is noted that the subset may include any number of groups and that each of the group may include any number of stimuli of any type. These and other parameters of the subset and the selected stimuli may be determined based on, for example, the initial screening and the personal information of the user, and optionally also based on the calibration results of a gaze tracking device of the system. These and other parameters of the subset may be further updated using an adaptive method, based on the feedback from the user up to that point of testing time.

The user may view the stimuli of the subset being displayed on the display, and a gaze of the user may move with respect to the display accordingly. A gaze tracking device (e.g., such as gaze tracking device 140, 240 described above with respect to FIGS. 1 and 2, respectively) may track the gaze of the user with respect to at least some of the stimuli of the subset being displayed on the display. In various embodiments, the gaze tracking device or the processing unit may generate at least one gaze dataset for at least some of the stimuli of the subset being displayed to yield multiple gaze datasets.

The processing unit may correlate at least one of the gaze datasets with the respective at least one stimulus of the subset (e.g., the stimulus/stimuli for which the at least one gaze dataset has been generated). For example, the processing unit may correlate, for at least one of the gaze datasets and for the respective at least one stimulus of the subset, a location of determined gaze point(s) (e.g., indicating an intersection of the gaze vector(s) with the display) with known location(s) of the gap of the respective at least one stimulus on the display (e.g., as described above with respect to FIGS. 4G, 4H, 4I, 4J, 4K, 4L, 4M, 4N, 4O, 4P, 4Q, 4R, 4S and 4T).

The processing unit may evaluate the vision of the user based on the correlation thereof. In some embodiments, the processing unit may determine a refractive error for the user based on the correlation thereof. In some embodiments, the processing unit may determine a prescription, or at least one prescription component for a user's eyewear based on the determined refractive error of the user.

In some embodiments, the processing unit may determine, based on at least one of the gaze datasets, at least one additional gaze dataset. The additional gaze dataset(s) may, for example, include at least one of: a number of fixation events, time intervals to the fixation events, saccades, distances between the gaps of sequential stimuli, distribution of the gaze points, rate of change in pupil constriction, rate of change in pupil dilation, and blink events. Changes in rates of pupil size may, for example, indicate cognitive load, which may be higher when the user is straining to determine the gap location. The pupil size, or rate of change of pupil diameter may, for example, correlate with gap size and/or refraction. In some embodiments, the processing unit may evaluate the vision of the user further based on the at least one additional gaze dataset.

In some embodiments, the processing unit may update the subset of stimuli during the evaluation of the vision of the user. The subset of the stimuli may be updated based on, for example, a response of the user to the stimuli being displayed on the display. For example, a probability that the user has perceived of the gap of the stimulus being displayed may be calculated based on the respective at least one gaze dataset, or combination of datasets, and next stimulus to be displayed may be then determined. In some embodiments, the processing unit may estimate (e.g., using an adaptive psychophysical procedure) a minimum perceivable size threshold of the gap in each axis (e.g., the smallest perceivable gap in the optotype). For example, the processing unit may use a staircase method that may test various gap sizes. In this manner, the gap size of the stimuli may be selected in a more refined way such that the user begins to respond to the stimuli consistently with errors.

Figure 5:
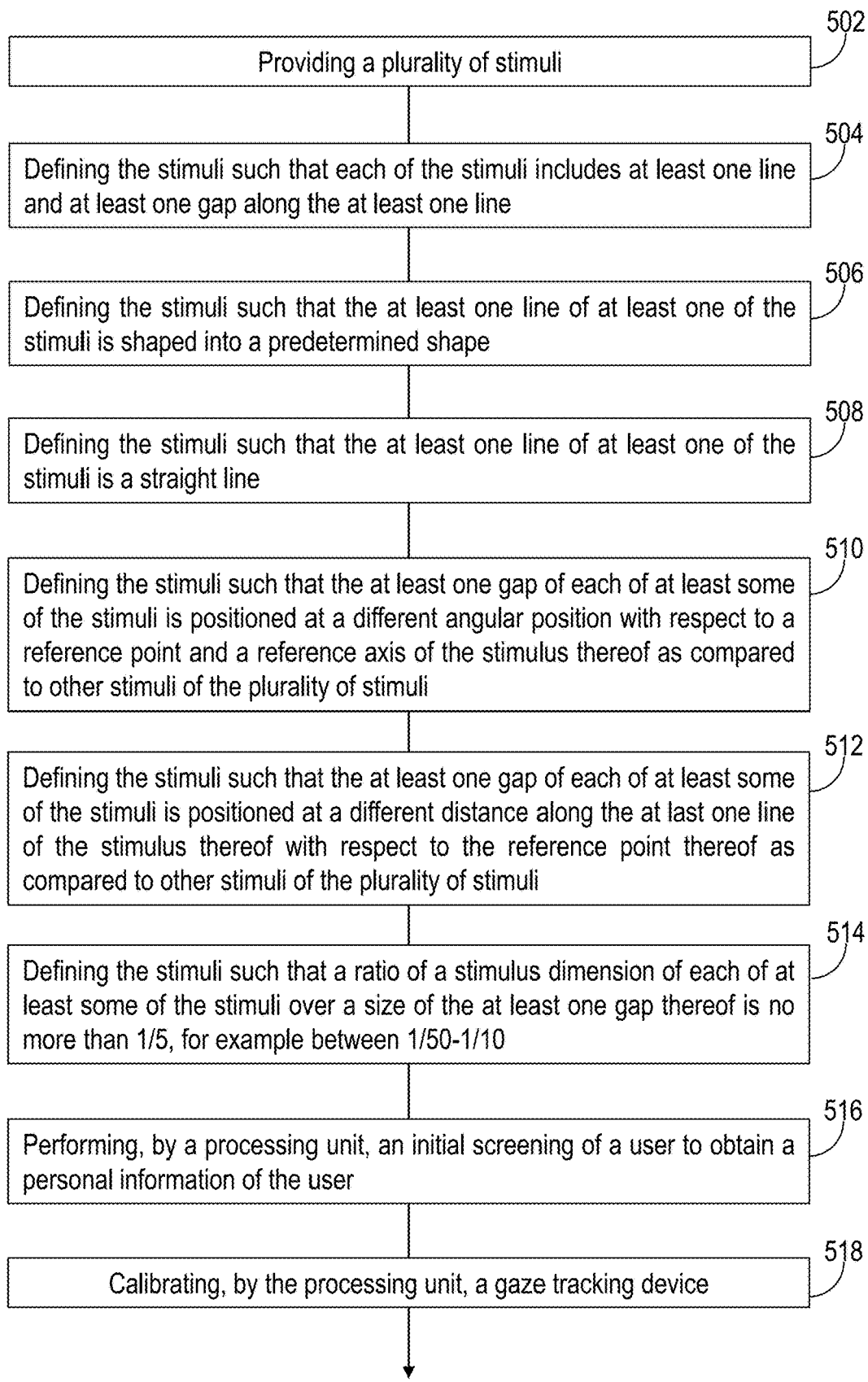
FIG. 5 is a flowchart of a method of automatically evaluating a vision of a user, according to some embodiments of the invention.

Reference is now made to FIG. 5, which is a flowchart of a method of automatically evaluating a vision of a user, according to some embodiments of the invention.

The method may be implemented by a system for automatically evaluating a vision of a user (e.g., such as system 100 and/or system 200 described above with respect to FIGS. 1 and 2, respectively), which may be configured to implement the method. It is noted that the method is not limited to the flowcharts illustrated in FIG. 5 and to the corresponding description. For example, in various embodiments, the method needs not move through each illustrated box or stage, or in exactly the same order as illustrated and described.

Some embodiments may include providing a plurality of stimuli (stage 502). For example, stimuli as described above with respect to FIG. 1 and FIGS. 4A, 4B, 4C, 4D, 4E and 4F.

Some embodiments may include defining the stimuli such that each of the stimuli includes at least one line and at least one gap along the at least one line (stage 504). For example, as described above with respect to FIGS. 4A, 4B, 4C, 3D, 3E and 4F.

Some embodiments may include defining the stimuli such that the at least one line of at least one of the stimuli is shaped into a predetermined shape (stage 506). For example, as described above with respect to FIGS. 4A, 4C, 4D.

Some embodiments may include defining the stimuli such that the at least one line of at least one of the stimuli is a straight line (stage 508). For example, as described above with respect to FIGS. 4B, 4E, 4F.

Some embodiments may include defining the stimuli such that the at least one gap of each of at least some of the stimuli is positioned at a different angular position with respect to a reference point and a reference axis of the stimulus thereof as compared to other stimuli of the plurality of stimuli (stage 510). For example, as described above with respect to FIGS. 4A, 4C, 4D.

Some embodiments may include defining the stimuli such that the at least one gap of each of at least some of the stimuli is positioned at a different distance along the at last one line of the stimulus thereof with respect to the reference point thereof as compared to other stimuli of the plurality of stimuli (stage 512). For example, as described above with respect to FIGS. 4B, 4E, 4F.

Some embodiments may include defining the stimuli such that a ratio of a stimulus dimension of each of at least some of the stimuli over a size of the at least one gap thereof is no more than 1/5, for example between 1/50-1/10 (stage 514). For example, as described above with respect to FIGS. 4A, 4B, 4C, 34D, 4E and 4F.

Some embodiments may include performing, by a processing unit, an initial screening of a user to obtain a personal information of the user (stage 516). For example, processing unit 130, 230 as described above with respect to FIGS. 1 and 2, respectively, and initial screening and personal information as described above with respect to FIG. 1.

Some embodiments may include calibrating, by the processing unit, a gaze tracking device (stage 518). For example, gaze tracking device 140, 240 as described above with respect to FIGS. 1 and 2, respectively, and calibration as described above with respect to FIG. 1.

Some embodiments may include selecting, determining or predetermining, by the processing unit, a subset of stimuli of the plurality of stimuli to be displayed to a user (stage 520). For example, as described above with respect to FIG. 1.

Some embodiments may include determining the subset of stimuli based on at least one of: the initial screening of the user and the calibration of the gaze tracking device (stage 522). For example, as described above with respect to FIG. 1 and FIGS. 4A-4T.

Some embodiments may include determining the subset of stimuli by randomly selecting the stimuli from the plurality of stimuli (stage 524). For example, as described above with respect to FIG. 1.

Some embodiments may include subsequently displaying, by the processing unit, on a display, the stimuli of the subset such that each of the stimuli is displayed in a predetermined order and for a predetermined stimulus-display time interval (stage 526). For example, display 120, 220 described above with respect to FIGS. 1 and 2, respectively.

Some embodiments may include determining, by the processing unit, the order and the stimulus-display time interval based on at least one of: the initial screening of the user and the calibration of the gaze tracking device (stage 528). For example, as described above with respect to FIG. 1 and FIGS. 4A-4T.

Some embodiments may include setting the stimulus-display time interval to range between 100-1500 milliseconds (stage 529). For example, as described above with respect to FIG. 1.

Some embodiments may include tracking, by the gaze tracking device, a gaze of the user with respect to at least some of the stimuli of the subset being displayed on the display (stage 530). For example, as described above with respect to FIGS. 1 and 2.

Some embodiments may include generating, by the gaze tracking device or by the processing unit, at least one gaze dataset for at least some of the stimuli of the subset being displayed to yield multiple gaze datasets (stage 532). For example, as described above with respect to FIGS. 1 and 2.

Some embodiments may include calculating, by the processing unit or by the gaze tracking device, for each of the gaze datasets, at least one of: a reference vector, a gaze vector, a gaze angle and a gaze point (stage 534). For example, reference vector 302, gaze vector 304, gaze angle 306 and gaze point 308, respectively, as described above with respect to FIG. 3.

Some embodiments may include receiving the gaze datasets from a remote processor (stage 535). For example, the gaze datasets may be calculated on a cloud based on readings of the gaze tracking device (e.g., as described above with respect to FIG. 1).

Some embodiments may include evaluating a vision of the user based on at least one of the gaze datasets (stage 536). For example, as described above with respect to FIG. 1.

Some embodiments may include correlating, by the processing unit, at least one of the gaze datasets with the respective at least one stimulus of the subset stimuli for which the at least one gaze dataset has been generated (stage 537). For example, as described above with respect to FIG. 1.

Some embodiments may include correlating, by the processing unit, for at least one of the gaze datasets and for the respective at least one stimulus of the subset, a location of determined at least one gaze point on the display with known at least one location of the respective at least one stimulus (or of at least a portion thereof) on the display (stage 538). For example, as described above with respect to FIG. 1 and FIGS. 4A-4T.

Some embodiments may include correlating, by the processing unit, for at least one of the gaze datasets and for the respective at least one stimulus of the subset, a location of determined at least one gaze point on the display with known at least one location of the at least one gap of the respective at least one stimulus on the display (stage 540). For example, as described above with respect FIGS. 4G-4T.

Some embodiments may include updating the subset of stimuli during the evaluation of the vision of the user based on at least one of the gaze datasets (stage 542).

Some embodiments may include updating the subset of stimuli by selecting and adding at least one additional stimulus of the plurality of stimuli to the subset, based on the correlation between at least one gaze dataset with the respective at least one stimulus that has been displayed on the display (stage 544). In this manner, the subset of stimuli may be updated in a staircase manner, wherein new one or more stimuli to be displayed are selected based on the response of the user to one or more previous stimuli that has been displayed (e.g., as described above with respect to FIG. 1 and FIGS. 4A-4T).

Some embodiments may include evaluating the vision of the user based on the correlation (stage 546). For example, as described above with respect to FIG. 1.

Some embodiments may include evaluating the vision of the user based on at least one of the gaze datasets using one or more artificial intelligence methods (stage 547). For example, as described above with respect to FIG. 1.

Some embodiments may include determining a refractive error for the user (e.g., based on the correlation) (stage 548). For example, as described above with respect to FIG. 1.

Some embodiments may include determining at least one of: one or more components of a prescription of a user's eyewear based on the determined refractive error of the user, a visual acuity of the user, a reaction time, and a contrast sensitivity (e.g., based on the correlation) (stage 550). For example, as described above with respect to FIG. 1.

Some embodiments may include determining, by the processing unit, based on at least one of the gaze datasets, at least one additional gaze dataset (stage 552). The additional gaze dataset(s) may, for example, include at least one of: a number of fixation events, time intervals to the fixation events, saccades, distances between the gaps of sequential stimuli, distribution of the gaze points, rate of change in pupil constriction, rate of change in pupil dilation, and blink events.

Some embodiments may include evaluating, by the processing unit, the vision of the user further based on the at least one additional gaze dataset (stage 554).

Advantageously, the disclosed system and method may provide an objective evaluation of a vision of a user. Specifically, the user may merely observe the stimuli being displayed on the screen, without providing any active input concerning the observed stimuli. The processing of the gaze data in response to the displayed stimuli may be automatically performed by the system, thus providing objective evaluation of the vision of the user. In this manner, the disclosed system and method may enable evaluation of the vision of the user which is independent of a cognitive condition of the user, not affected by a subjective interpretation of the stimuli by the user, enables evaluation of the vision through the multiple stages thereof and reduces the overall testing time as compared to current electronical systems.

Due to the ability to measure the user's response during a short display time, the overall testing time is faster, and large datasets can be obtained in a few minutes. This is a significant advantage over existing automatic refraction tools, that can take up to 40 minutes. Decreased testing time and objective measurements (e.g., that do not require an active user response) make it easier for the user to perform the test and reduces user fatigue.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions thereof. The computer program instructions can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams can represent a module, segment, or portion of code, which includes one or more executable instructions for implementing the specified logical function(s). It should also be noted that, in some alternative implementations, the functions noted in the portion can occur out of the order noted in the figures. For example, two portions shown in succession can, in fact, be executed substantially concurrently, or the portions can sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method of automatically evaluating a vision of a user, the method comprising:
displaying, by a processing unit, on a display, a subset of stimuli of a plurality of stimuli such that each of the stimuli is displayed for a predetermined stimulus-display time interval;
tracking, by a gaze tracking device, a gaze of the user with respect to at least some of the stimuli of the subset being displayed on the display;
obtaining multiple gaze datasets, at least one gaze dataset for at least some of the stimuli of the subset being displayed; and
evaluating, by the processing unit, the vision of the user based on at least one of the multiple gaze datasets by determining at least one of: a refractive error of the user, one or more components of a prescription of a user's eyewear based on the determined refractive error of the user, a visual acuity of the user, a reaction time, and a contrast sensitivity.

2. The method of claim 1, further comprising:
correlating, by the processing unit, at least one of the multiple gaze datasets with the respective at least one stimulus of the subset stimuli for which the at least one gaze dataset has been generated; and
evaluating the vision of the user based on the correlation thereof.

3. The method of claim 1, further comprising obtaining the multiple gaze datasets is by at least one of: calculating the multiple gaze datasets by the processing unit, calculating the multiple gaze datasets by the gaze tracking device; and receiving the multiple gaze datasets from a remote processor.

4. The method of claim 1, further comprising:
performing, by the processing unit, an initial screening of a user to obtain a personal information of the user; and
determining at least one of: the subset of the stimuli, the order in which the stimuli to be displayed and the stimulus-display time interval, based on the initial screening of the user.

5. The method of claim 1, further comprising updating, by the processing unit, the subset of stimuli by selecting and adding at least one additional stimulus of the plurality of stimuli to the subset, based on at least one of the multiple gaze datasets.

6. The method of claim 1, further comprising setting, by the processing unit, the stimulus-display time interval to range between 100-1500 milliseconds.

7. The method of claim 1, further comprising defining the stimuli such that each of the stimuli includes at least one line and at least one gap along the at least one line and such that a ratio of a stimulus dimension of each of at least some of the stimuli over a size of the at least one gap thereof ranges between 1/50-1/10.

8. The method of claim 7, further comprising:
correlating, by the processing unit, for at least one of the gaze datasets and for the respective at least one stimulus of the subset, a location of a determined at least one gaze point on the display with known at least one location of the at least one gap of the respective at least one stimulus on the display; and
evaluating the vision of the user based on the correlation thereof.

9. A system for automatically evaluating a vision of a user, the system comprising:
a display configured to display a subset of stimuli of a plurality of stimuli such that each of the stimuli is displayed in a predetermined order and for a predetermined stimulus-display time interval;
a gaze tracking device configured to track a gaze of the user with respect to at least some of the stimuli of the subset being displayed on the display, and
a processing unit configured to:

obtain multiple gaze datasets, at least one gaze dataset for at least some of the stimuli of the subset being displayed, and evaluate the vision of the user based on at least one of the multiple gaze datasets; and determine at least one of: a refractive error of the user, one or more components of a prescription of a user's eyewear based on the determined refractive error of the user, a visual acuity of the user, a reaction time, and a contrast sensitivity.

10. The system of claim 9, wherein the processing unit is further configured to obtain the multiple gaze datasets by at least one of: calculating the multiple gaze datasets, receiving the multiple gaze datasets from the gaze tracking device, and receiving the multiple gaze datasets from a remote processor.

11. The system of claim 9, wherein the processing unit is further configured to:

perform an initial screening of a user to obtain a personal information of the user; and determine at least one of: the subset of the stimuli, the order in which the stimuli to be displayed and the stimulus-display time interval, based on the initial screening of the user.

12. The system of claim 9, wherein the processing unit is further configured to update the subset of stimuli by selecting and adding at least one additional stimulus of the plurality of stimuli to the subset, based on at least one of the multiple gaze datasets.

13. The system of claim 9, wherein the processing unit is further configured to set the stimulus-display time interval to range between 100-1500 milliseconds.

14. The system of claim 9, wherein each of the stimuli comprises at least one line and at least one gap along the at least one line, wherein a ratio of a stimulus dimension of each of at least some of the stimuli over a size of the at least one gap thereof ranges between 1/50-1/10.

15. The system of claim 14, wherein the processing unit is further configured to:

correlate, by the processing unit, for at least one of the gaze datasets and for the respective at least one stimulus of the subset, a location of determined at least one gaze point on the display with known at least one location of the at least one gap of the respective at least one stimulus on the display; and evaluate the vision of the user based on the correlation thereof.

16. A system for automatically evaluating a vision of a user, the system comprising:

a display configured to display a subset of stimuli of a plurality of stimuli;

a gaze tracking device configured to track a gaze of the user with respect to at least some of the stimuli of the subset being displayed on the display, and a processing unit configured to:

obtain multiple gaze datasets, at least one gaze dataset for at least some of the stimuli of the subset being displayed, and determine, based on at least one of the multiple gaze datasets, at least one of: a refractive error of the user, one or more components of a prescription of a user's eyewear based on the determined refractive error of the user, a visual acuity of the user, a reaction time, and a contrast sensitivity.

17. The system of claim 16, wherein the processing unit is further configured to:

perform an initial screening of a user to obtain a personal information of the user; and determine the subset of the stimuli based on the initial screening of the user.

18. The system of claim 16, wherein the processing unit is further configured to update the subset of stimuli based on at least one of the multiple gaze datasets indicative of a user's response to at least one of previously displayed stimuli.

19. The system of claim 16, wherein the processing unit is configured to display each of the stimuli of the set for a time interval ranging between 100-1500 milliseconds.

20. The system of claim 16, wherein each of the stimuli comprises at least one line and at least one gap along the at least one line, wherein a ratio of a stimulus dimension of each of at least some of the stimuli over a size of the at least one gap thereof ranges between 1/50-1/10.

* * * * *